United States Patent [19]

Gless, Jr.

[11] 4,358,612
[45] Nov. 9, 1982

[54] PROCESS FOR PRODUCTION OF α-HALOALKYLAMIDES

[75] Inventor: Richard D. Gless, Jr., Oakland, Calif.

[73] Assignee: Stauffer Chemical Company, Westport, Conn.

[21] Appl. No.: 294,101

[22] Filed: Aug. 21, 1981

Related U.S. Application Data

[63] Continuation-in-part of Ser. No. 222,210, Jan. 2, 1981, abandoned.

[51] Int. Cl.³ .......................................... C07C 102/06
[52] U.S. Cl. .................................. 564/137; 260/404; 564/135
[58] Field of Search ................. 564/137, 135; 260/404

[56] References Cited

U.S. PATENT DOCUMENTS

| | | | |
|---|---|---|---|
| 2,268,129 | 12/1941 | Reppe et al. | 564/137 |
| 3,655,690 | 4/1972 | Hobbs et al. | 564/137 |
| 3,763,234 | 10/1973 | Brill | 564/137 |
| 4,258,200 | 3/1981 | Daughenbaugh | 564/131 |
| 4,259,259 | 3/1981 | McEntire | 564/137 |

FOREIGN PATENT DOCUMENTS 2042503 9/1980 United Kingdom.

OTHER PUBLICATIONS

Yazawa et al., Tet. Letters, 1964, #46, pp. 3955–3956.
Chandra et al., J. Chem. Soc. ©1969, pp. 2565–2568.
Snatzke, Chem. Ber. 1973, 106, pp. 2072–2075.
Organic Synthesis, Coll.-vol. 1, 2nd Edition, pp. 153–154.

Primary Examiner—Arthur P. Demers
Attorney, Agent, or Firm—Joel G. Ackerman

[57] ABSTRACT

Amides having the formula $$RCONR_2R_3$$

in which R is α-halo-$C_1$–$C_8$-alkyl; $R_2$ is $C_1$–$C_8$ alkyl, and $R_3$ is $C_1$–$C_8$ alkyl, are prepared by reacting an ester with an amine in the presence of a promotor which is a halide of a Group IIIa metal having a molecular weight of 26 or greater, or of a Group IVb metal. The process is particularly suitable for production of a desired optical isomer of such an amide.

13 Claims, No Drawings

PROCESS FOR PRODUCTION OF α-HALOALKYLAMIDES

CROSS REFERENCE TO RELATED APPLICATIONS

This is a continuation-in-part of commonly assigned U.S. patent application Ser. No. 222,210, filed Jan. 2, 1981, now abandoned.

BACKGROUND AND PRIOR ART

This invention relates to a process for production of amides by reaction of an ester with an amine in the presence of a substance which promotes this reaction. The reaction is generally described by the following formula $$RCOOR_1 + R_2R_3NH \xrightarrow[\text{prom.}]{} RCONR_2R_3 + R_1OH$$

in which R is α-halo-$C_1$–$C_8$-alkyl; $R_1$ is $C_1$–$C_8$ alkyl; and $R_2$ and $R_3$ are $C_1$–$C_8$ alkyl, and may be the same or different alkyl groups.

The term "alkyl" includes both straight and branched chain groups of this type. The term "α-halo-$C_1$–$C_8$ alkyl" includes both straight and branched chain alkyl groups having a halogen atom (chlorine, fluorine, or bromine, preferably chlorine) bonded to the carbon atom adjacent (α) to the carboxyl moiety. The alkyl portion of this haloalkyl moiety may optionally be substituted by additional halogen atoms, bonded to other carbon atoms.

In a preferred embodiment, the products of the process of this invention are optically active amides; in the most preferred embodiment the α-carbon atom (to which the halogen is bonded) is optically active. In further preferred embodiments, R is α-halo-$C_1$–$C_4$-alkyl, $R_1$ is $C_1$–$C_4$-alkyl, $R_2$ is $C_2$–$C_4$ alkyl and $R_3$ is $C_1$–$C_4$ alkyl.

The substances which have been found suitable for promoting this reaction are selected from the group consisting of halides of metals in Group IIIa having a molecular weight of 26 or greater, and of metals in Group IVb. Of the Group IIIa metal halides, those of aluminum, particularly aluminum trichloride and aluminum tribromide, are preferred. Of those of Group IVb, halides of titanium and zirconium, particularly the tetrachlorides, and most preferably zirconium tetrachloride, are preferred.

In its most preferred form, the present process provides a method for the preparation of optically active amides of lower α-haloalkyl carboxylic acids. Most preferably, the process relates to the production of L-N,N-diethyl-2-halopropionamides, and particularly to the chloropropionamides of this type, by a one-step preparation from the corresponding L-(lower alkyl)-2-halopropionate, preferably from an L-methyl2-halopropionate.

Some methods for the production of such compounds are given in the article by Snatzke, et al., Chem. Ber., 106, pp. 2072-2075 (1973). These include the reaction of optically active lactic acid with thionyl chloride and reaction of alanines with sodium nitrite in the presence of HCl or HBr. The former process produces the desired compound in only about 23% yield; the latter process requires several steps.

The reaction of esters with amines to produce amides is well known in the prior art. One example is the article by Yazawa, Tetrahedron Letters, No. 46, pp. 3995-3996 (1974), which describes the reaction of esters and amines in the presence of boron tribromide to produce amides. Another article of interest is the publication by Chandra, et al., J. Chem. Soc. (C), 1969, pp. 2565-2568, which describes the reaction of carbonyl compounds, including carboxylic acids, anhydrides, and esters, with a metal amide, particularly a titanium amide. Alternatively, it is suggested to use a complex formed by reaction of titanium tetrachloride with a secondary amine. Such a process requires either the production or purchase of the metal amide, which is rather expensive, and also requires at least two steps.

U.S. Pat. No. 3,655,690 relates to the production of certain amides by reaction of a carboxylic acid or salt thereof with an amine. Certain metal halides are said to be useful as catalysts for the reaction. U.S. Pat. No. 3,763,234 describes a process for production of amides by reaction of esters and amines in the presence of Lewis acids, preferably uranium salts, as catalysts. In this process, the Lewis acid is used in at least 0.005 mole %. Reaction times are said to vary from 0.1 to 48 hours. The statement is made that use of the Lewis acid in amounts greater than 25 mole % provides "no particular advantage."

SUMMARY OF THE INVENTION

In brief, this invention relates to a process for production of amides having the formula $$RCONR_2R_3$$

in which R is α-halo-$C_1$–$C_8$-alkyl, and $R_2$ and $R_3$ are $C_1$–$C_8$ alkyl, by reaction of an ester having the formula $$RCOOR_1$$

in which R is as above defined and $R_1$ is $C_1$–$C_8$ alkyl, with an amine having the formula $$R_2R_3NH$$

in which $R_2$ and $R_3$ are as above defined, in the presence of from about 50 to about 300 mole %, based on the ester, of a promoter comprising a halide of a Group IIIa metal having an atomic weight of 26 or greater, or of a Group IVb metal.

In a preferred embodiment, this invention relates to a process for the production of amides having the formula $$RCONR_2R_3$$

in which R is α-halo-$C_1$–$C_4$-alkyl, $R_2$ is $C_2$–$C_4$ alkyl, and $R_3$ is $C_1$–$C_4$ alkyl, by reaction of an ester having the formula $$RCOOR_1$$

in which $R_1$ is $C_1$–$C_4$ alkyl, with an amine having the formula $$R_2R_3NH$$

(R, $R_2$ and $R_3$ being as above defined) in the presence of from about 50 to about 300 mole %, based on the ester, of a promoter comprising a halide of a metal of Group IIIa having an atomic weight of 26 or greater, or of a metal metal of Group IVb.

In its most preferred embodiment, this invention relates to a process for the production of compounds, particularly optically active compounds, having the formula $RCONR_2R_3$ in which R is 1-haloethyl and $R_2$ and $R_3$ are each ethyl, by reaction of a compound having the formula $RCOOR_1$ in which R is 1-haloethyl and $R_1$ is methyl, with diethylamine, in the presence of an aluminum trihalide, a zirconium tetrahalide or a titanium tetrahalide, in an amount as specified herein.

DETAILED DESCRIPTION OF THE INVENTION

The amides which can be produced by this process are useful as intermediates in a number of processes.

The 2-halopropionamides, particularly the N,N-diethyl-2-chloro- or bromo-propionamides, have been particularly found useful as chemical intermediates in the preparation of α-naphthoxy alkyl amides by reaction with α-naphthol and sodium methoxide or an alkali metal hydroxide, as described for instance in U.S. Pat. Nos. 3,480,671, 3,718,455 and 3,998,880. The compound D-(−)-N,N-diethyl-2-(α-naphthoxy)propionamide is particularly active as a herbicide. This compound, and a method for its preparation are described in U.S. Pat. No. 3,718,455. In that process, racemic 2-(α-naphthoxy)propionic acid was resolved into its optical isomers, which were then individually converted to the acyl chlorides and reacted with diethylamine to produce the optical isomers of the amide.

The present process provides a method for producing the L isomer L-N,N-diethyl-2-chloro- or bromo-propionamide from the corresponding L-methyl-2-chloro- or bromo-propionate in one step, and in good overall yield, as well as excellent yield of the L-isomer itself. Production of other optical isomers is dramatically decreased as opposed to the prior art methods.

In the conduct of the reaction, in general, a flask or vessel fitted with a nitrogen or other inert gas sweep and a means for adding the promoter is charged with the ester, the amine, and a solvent. The solvent may be one of the usual organic solvents which have no reactive functional groups. Some examples are methylene chloride and aromatic hydrocarbon solvents such as toluene.

The promoter, preferably as an anhydrous powder, is then added to the mixture over a period of time to permit temperature control, if necessary. The addition of the promoter is generally performed over a time between 1 minute and 1 hour, preferably between 1 and 25 minutes.

The reaction time, starting from the end of addition of the promoter, will generally be from about 10 minutes to as long as several hours, with extended times having no demonstrated effect on yields or optical purity. Preferably, reaction times are 10–60 minutes.

Temperature of the reaction mixture is generally maintained from about −20° to about +150° C., preferably from about 5° to about 50° C.

In general, the amine is employed in the amount of from about 100 to about 600 mole % based on the ester, with the promoter being employed in an amount (relative to the ester), depending on the promoter used, as follows: halides of Group IIIa metals, for instance, aluminum trihalides—from about 67 to about 200 mole %; halides of Group IVb metals—from about 50 to about 300 mole %; more specifically, zirconium tetrahalides—from about 50 to about 200 mole%, and titanium tetrahalides—from about 100 to about 300 mole %.

The order of mixing the ester and amine is generally not material in carrying out the process; however, when utilizing optically active reagents, a better optical yield may be obtained if the halide promoter is first mixed with the amine in a solvent, and this mixture is then added to the ester.

After the reaction is complete, the reaction mixture is washed with aqueous acid, dried over a drying agent such as magnesium sulfate and the solvent is evaporated to provide the desired product.

The use of the promoters, in the amounts mentioned above, results in advantages over the prior art, particularly U.S. Pat. No. 3,763,234, in that substantially higher yields of the desired product (50–95% of theoretical) are obtained (as compared to about 30%), with substantially shorter reaction times. Additionally, the promoter, used in the amount specified, further serves to take up the alcohol produced, eliminating the step or steps required to separate this by-product.

The following examples illustrate the conduct of the process as applied to the preparation of L-(+)-N,N-diethyl-2-chloropropionamide, by the reaction of L-(−)-methyl-2-chloropropionate and L-(−)-isobutyl-2-chloropropionate, with diethyl amine. However, as mentioned previously, these examples are merely intended to illustrate the conduct of the reaction, and the process described herein can be applied to the production of a larger class of amides, including both those which are optically active and those which do not possess optical activity.

EXAMPLE 1

This example illustrates the conduct of the process using aluminum chloride as a promoter.

In a flask equipped with an argon sweep, there were placed 8.84 ml. (10.0 g., 0.0817 mole) L-(−)-methyl2-chloropropionate (95% L isomer), 16.9 ml. (12.0 g., 0.163 mole) diethyl amine and 50 ml. toluene. There was then added 7.4 g. (0.055 mole) aluminum chloride, through a Gooch tube, over a period of 13 minutes, with cooling. The temperature of the reaction mixture was 27° C. at the end of the addition.

After 50 minutes, the reaction mixture was added to 100 ml. of 3 M HCl. The mixture temperature rose to 35° C. The organic phase was separated, the aqueous acid phase was washed with 50 ml. toluene, the organic extracts were combined and washed with 50 ml. saturated aqueous sodium chloride, dried over magnesium sulfate, filtered and stripped of solvent to produce 11.86 g. of a water-white crude liquid which did not discolor on standing.

Of this product, 11.5 g. was distilled at 105°–108° C. and 10 mm. Hg yielding 9.88 g. of N,N-diethyl-2-chloropropionamide, which was analyzed by gas chromatography at 97.5% purity. This corresponds to 74% yield of theoretical.

Analysis of the product by nuclear magnetic resonance (nmr) spectroscopy determined that the ratio of L to D isomers was 88:12.

EXAMPLE 2

This example demonstrates the conduct of the process using zirconium tetrachloride as the promoter.

In a flask was placed 8.41 ml. (9.5 g., 0.077 mole) L-(−)-methyl-2-chloropropionate (95% L isomer), 17 ml. (12.1 g., 0.165 mole) diethyl amine and 50 ml. methylene chloride. There was then added, over a period of 30 minutes, 18.1 g. (0.077 mole) zirconium tetrachloride. The reaction mixture changed color from bright yellow to brownish yellow to reddish brown as the reaction proceeded. Temperature was maintained at about 10°–20° C. Forty minutes after the end of the addition of the zirconium tetrachloride the reaction mixture was poured into 100 ml. of 3 N HCl. Some heat evolved, resulting from the decomposition of zirconium salts. The layers were separated and the aqueous layer extracted with 50 ml. methylene chloride. The organic layers were combined, dried and stripped, as in Example 1, producing 10.77 g. of a light orange oil. This was distilled at 102°–104° C. at 4 mm. Hg producing 9.29 g. (75% of theoretical yield) of N,N-diethyl-2chloropropionamide.

The optical rotation of the product was determined in 10 ml. chloroform in a 20 cm. cell to show a ratio of L:D isomers of 87:13, corresponding to a 91.7% optical yield of the L-isomer.

EXAMPLE 3

This example illustrates the use of titanium tetrachloride as a promoter for this process.

In a flask with an argon sweep were placed 8.6 ml. (9.72 g., 0.079 mole) L-(−)-methyl-2-chloropropionate (95% L isomer), 17 ml. (12 g., 0.164 mole) diethyl amine and 40 ml. methylene chloride. There was then added, over a seven-minute period, 15.5 g. (0.082 mole) titanium tetrachloride. A violent exotherm occurred during the addition of the first two-thirds of the catalyst, with essentially no exotherm during the addition of the last one-third. Temperature of the reaction mixture was maintained below 27° C., generally between about 10° and 20° C. A black-green solution resulted; it was poured into 100 ml. of 1 M HCl. The organic phase was separated and the aqueous phase washed with two portions each of 50 ml. methylene chloride. The organic layers were combined, dried over magnesium sulfate, filtered and stripped of solvent. The resulting product was distilled at 91°–92° C. and 5 mm. Hg, producing 6.70 g. of a water-white liquid, determined by analysis to be 96.9% N,N-diethyl-2-chloropropionamide (51% of theoretical yield). The ratio of L:D isomers was determined to be 57:43.

EXAMPLE 4

This example illustrates the use of an isobutyl ester as a reactant.

In a flask, equipped with a nitrogen sweep, were placed 5.93 g. (0.045 mole) aluminum chloride and 50 ml. toluene. There was then added 13.75 ml. (0.133 mole) diethylamine, with the temperature during addition maintained below 50° C. After 10 minutes, 10.0 g (0.061 mole) L-(−)-isobutyl-2-chloropropionate (>95% L-isomer) was added, over 5 minutes, with the temperature maintained at 20°–25° C. After an additional 2.5 hours the mixture was washed with 75 ml. aqueous 3 M HCl and phase separated. There was recovered 54.6 g. of a toluene solution, which was shown by analysis to contain 16.8 weight % (92% of theoretical yield) L-(+)-N,N-diethyl-2-chloropropionamide. The ratio of L:D isomers was determined to be 95:5.

Other modifications and/or alternative embodiments of the process will be clear to those skilled in the art.

What is claimed is:

1. A process for the production of an optical isomer of an amide having the formula $$RCONR_2R_3$$

in which R is α-halo-$C_1$-$C_8$-alkyl; and $R_2$ and $R_3$ are the same or different $C_1$-$C_8$ alkyl, comprising reacting an ester having the formula $$RCOOR_1$$

in which $R_1$ is $C_1$-$C_8$ alkyl, with an amine having the formula $$R_2R_3NH$$

in the presence of from about 50 to about 300 mole %, based on the ester, of a promoter comprising a halide of a Group IIIa metal having an atomic weight of 26 or greater, or of a Group IVb metal.

2. A process according to claim 1 in which the amide has the L-(+) optical configuration.

3. A process according to claim 1 in which the optical activity lies at the α-carbon atom in the acid residue.

4. A process according to claim 1 in which $R_1$ is $C_1$-$C_4$ alkyl.

5. A process according to claim 1 in which R is α-halo-$C_1$-$C_4$-alkyl, $R_2$ is $C_1$-$C_4$ alkyl and $R_3$ is $C_2$-$C_4$ alkyl.

6. A process according to claim 5 in which R is α-haloethyl and $R_2$ and $R_3$ are each ethyl.

7. A process according to claim 6 in which the amide has the L-(+)-configuration.

8. A process according to claim 1 in which the promoter is an aluminum trihalide.

9. A process according to claim 8 in which the promoter is present in an amount of from about 67 to about 200 mole %, based on the ester.

10. A process according to claim 1 in which the promoter is a zirconium tetrahalide.

11. A process according to claim 10 in which the promoter is present in an amount of from about 50 to about 200 mole %, based on the ester.

12. A process according to claim 1 in which the temperature is from about 5° to about 50° C.

13. A process according to claim 1 in which the reaction time is from about 10 to about 60 minutes.

* * * * *